United States Patent
Daniel

(10) Patent No.: US 9,848,866 B2
(45) Date of Patent: *Dec. 26, 2017

(54) SYSTEM FOR IMPLANTING AN IMPLANTABLE PENILE PROSTHETIC

(71) Applicant: Coloplast A/S, Humlebaek (DK)

(72) Inventor: Geoffrey A. Daniel, Crystal, MN (US)

(73) Assignee: Coloplast A/S, Humlebaek (DK)

( * ) Notice: Subject to any disclaimer, the term of this patent is extended or adjusted under 35 U.S.C. 154(b) by 0 days.

This patent is subject to a terminal disclaimer.

(21) Appl. No.: 15/352,626

(22) Filed: Nov. 16, 2016

(65) Prior Publication Data

US 2017/0055974 A1 Mar. 2, 2017

Related U.S. Application Data

(63) Continuation of application No. 14/672,239, filed on Mar. 30, 2015, now Pat. No. 9,549,729.

(60) Provisional application No. 62/112,652, filed on Feb. 6, 2015.

(30) Foreign Application Priority Data

Jan. 29, 2016 (EP) .................................... 16153270

(51) Int. Cl.
| | |
|---|---|
| A61B 17/04 | (2006.01) |
| A61B 17/062 | (2006.01) |
| A61B 17/34 | (2006.01) |
| A61F 2/26 | (2006.01) |
| A61B 17/00 | (2006.01) |

(52) U.S. Cl.
CPC .......... *A61B 17/04* (2013.01); *A61B 17/0482* (2013.01); *A61B 17/0493* (2013.01); *A61B 17/062* (2013.01); *A61B 17/0625* (2013.01); *A61B 17/3468* (2013.01); *A61B 2017/00845* (2013.01); *A61F 2/26* (2013.01)

(58) Field of Classification Search
CPC ..... A61F 2/26; A61B 17/06066; A61B 17/04; A61B 2017/06052
USPC ...................................... 600/38–41; 128/898
See application file for complete search history.

(56) References Cited

U.S. PATENT DOCUMENTS

| | | | | |
|---|---|---|---|---|
| 5,980,539 A | * | 11/1999 | Kontos .............. | A61B 17/0482 606/144 |
| 6,322,570 B1 | * | 11/2001 | Matsutani .......... | A61B 17/0469 606/139 |
| 6,344,042 B1 | * | 2/2002 | Curtis ................ | A61B 17/0401 606/232 |
| 7,407,482 B2 | * | 8/2008 | Kuyava ..................... | A61F 2/26 600/40 |
| 7,699,857 B2 | * | 4/2010 | Kim ................... | A61B 17/0469 606/144 |
| 9,549,729 B2 | * | 1/2017 | Daniel ................... | A61B 17/04 |

* cited by examiner

*Primary Examiner* — Samuel Gilbert
(74) *Attorney, Agent, or Firm* — Coloplast Corp., Coloplast A/S; Nick Baumann

(57) ABSTRACT

A system for implanting an implantable penile prosthetic includes a tube with a bore formed in the tube, a first suture attached to a proximal portion of a needle, with the needle inserted in the bore, and with system characterized by an absence of a plunger inserted into the bore.

10 Claims, 14 Drawing Sheets

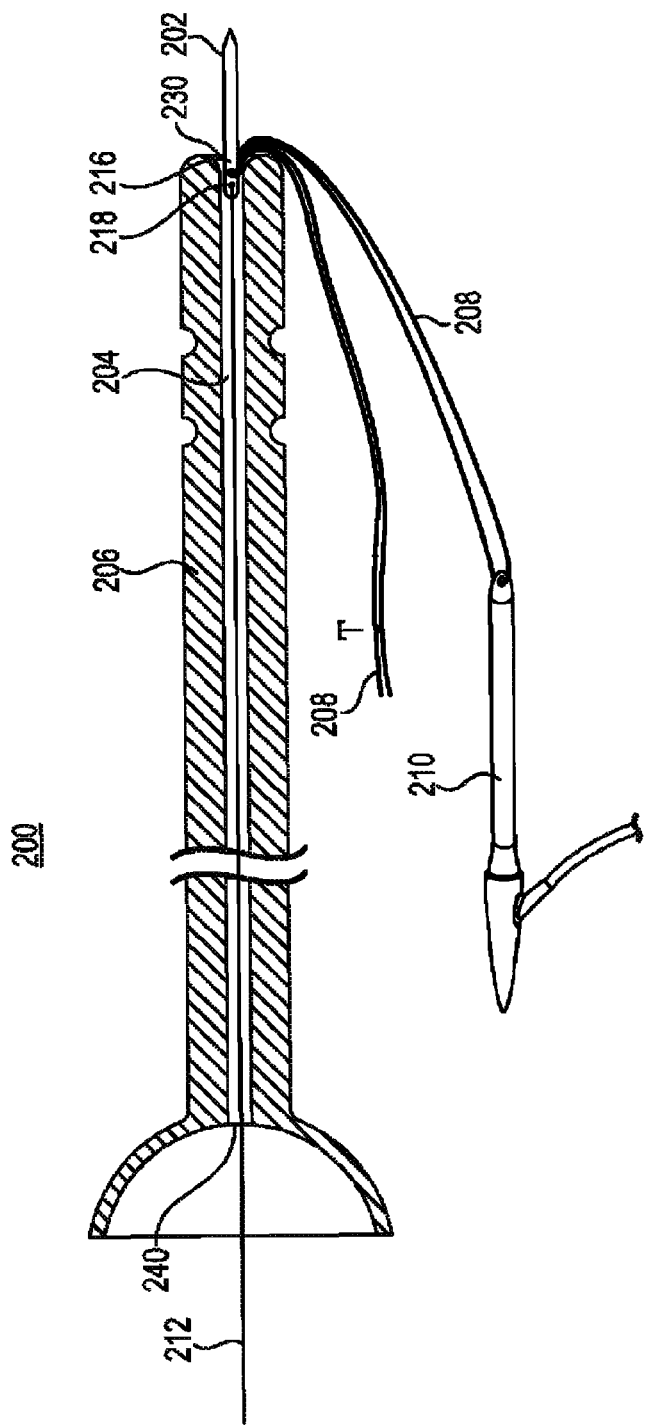
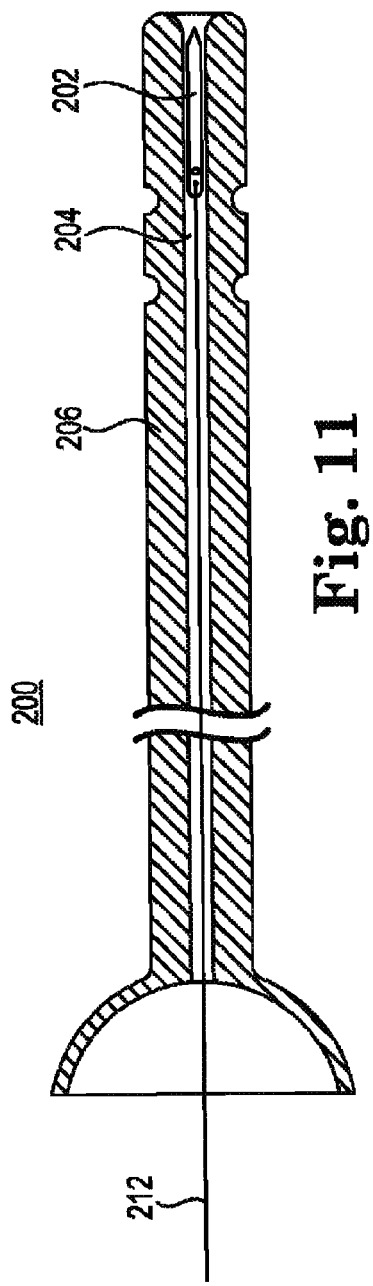

SYSTEM FOR IMPLANTING AN IMPLANTABLE PENILE PROSTHETIC

SUMMARY

One aspect provides a system for implanting an implantable penile prosthetic. The system includes a tool and a suture connected to a needle. The tool includes a tube extending between a handle portion and a distal end, and a bore formed in the tube. The bore forms a first opening at the distal end of the tube and a second opening located proximal of the distal end of the tube. A suture slide communicates with the bore and has a curved surface formed between an exterior surface of the tube and the bore of the tube. A first suture is attached to a proximal portion of a needle, with the needle inserted in the bore. A pointed distal end of the needle is closer to the first opening than to the second opening of the tube, and a segment of the first suture is inserted in the bore and alongside the needle. The first suture is in contact with the suture slide, and a proximal portion of the first suture extends out of the bore at the suture slide. The suture slide is located distal of the proximal portion of the needle that is retained in the bore. The system is configured such that tension applied to the first suture ejects the pointed distal end of the needle out of the distal end of the tube.

BRIEF DESCRIPTION OF THE DRAWINGS

The accompanying drawings are included to provide a further understanding of embodiments and are incorporated into and a part of this specification. The drawings illustrate embodiments and together with the description serve to explain principles of embodiments. Other embodiments and many of the intended advantages of embodiments will be readily appreciated as they become better understood by reference to the following detailed description. The elements of the drawings are not necessarily to scale relative to each other. Like reference numerals designate corresponding similar parts.

FIG. 10 is a cross-sectional view of the system illustrated in FIG. 9 with tension applied to the first suture to eject needle out of the bore of the tool and the second suture located in the bore of the tool.

FIG. 11 is a cross-sectional view of the system illustrated in FIG. 10 with the first suture and the prosthetic removed from the tool and the second suture employed to retract the needle back into the tool.

DETAILED DESCRIPTION

Figure 1:
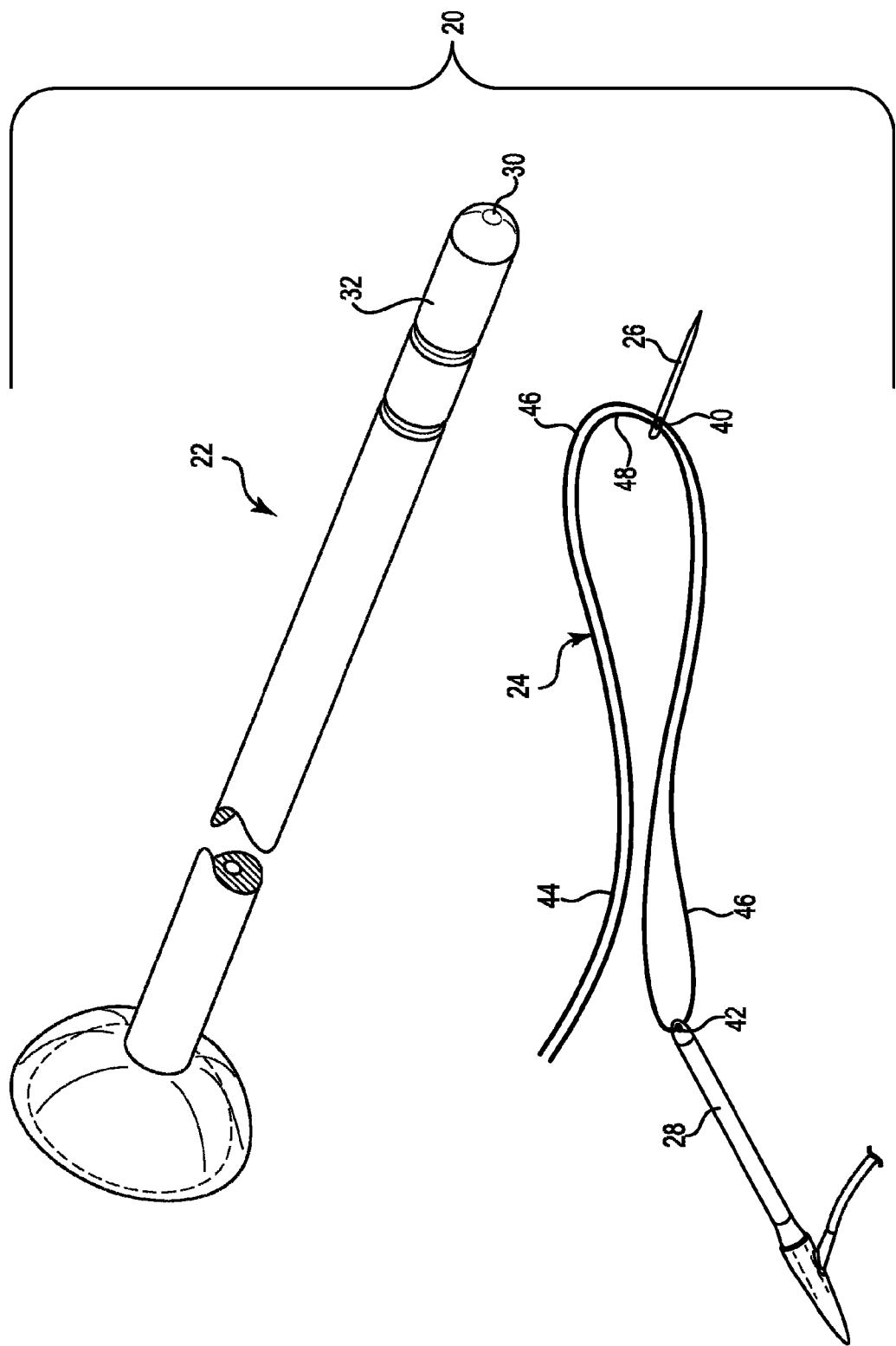
FIG. 1 is a perspective view of one embodiment of a system for implanting an implantable penile prosthetic including a needle and a tool.

In the following detailed description, reference is made to the accompanying drawings. The drawings form a part of this specification and illustrate exemplary embodiments for practicing the invention. Directional terminology, such as "top," "bottom," "front," "back," "leading," "trailing," etc., is used with reference to the orientation of the Figure(s) being described. Because components of embodiments can be positioned in a number of orientations, the directional terminology is used for purposes of illustration and is in no way limiting. It is to be understood that other embodiments may be utilized and structural or logical changes may be made without departing from the scope of the invention. The detailed description describes examples for practicing the invention and is not to be read to limit the scope of the invention. The scope of the invention is defined by the attached claims.

Embodiments, and features of the various exemplary embodiments described in this application, may be combined with each other ("mixed and matched"), unless specifically noted otherwise.

End means endmost. Relative to an observer, for example a surgeon, a distal end is the furthest endmost location of a distal portion of a thing being described, whereas a proximal end is the nearest endmost location of a proximal portion of the thing being described. The portion next to or adjacent to an end is an end portion.

An implanted penile prosthetic has proven useful in treating erectile dysfunction in men. One acceptable implantable penile prosthetic includes two inflatable cylinders implanted in the penis, a pump implanted in the scrotum or other internal space of the body, and a liquid holding reservoir implanted in the abdomen or other internal space of the body.

In an implantation procedure, the penis of the patient is incised in a corporotomy to expose a pair of corpora cavernosa that are aligned axially in a side-by-side orientation within the penis. A cutting implement, such as a curved Mayo scissors, is employed to penetrate the fascia of the penis and form an opening accessing each corpora cavernosum. Subsequently, each corpora cavernosum is dilated (opened) with an appropriate dilation tool to form a recess that is sized to receive one of the two cylinders of the penile prosthetic. Thereafter, a tool (referred to by surgical practitioners as a "Furlow" introducer) is inserted into each dilated corpora cavernosum to measure a length of the penis distally and proximally to determine a desired length of the cylinders to be implanted. A cylinder of the appropriately selected length is secured to a suture, and the suture is secured to a needle (sometimes called a "Keith" needle). The Keith needle is attached to the Furlow introducer. The Keith needle could possibly fall out of the Furlow introducer, so the surgical staff handles the tool with care. The surgeon steadies the Furlow introducer with one hand and pushes a plunger (or obturator) of the Furlow introducer with the other hand. Pushing the plunger pushes the needle from of the introducer, through tissue of the penis, and out the glans penis. The exposed portion of the needle is handled by the surgeon, removed from the suture, and discarded. The remaining suture is subsequently employed to tow the cylinder into place within the dilated corpora cavernosum.

The above-described procedure has proven effective when implanting penile prostheses. However, surgeons would appreciate having fewer parts to handle during the procedure. In addition, surgeons and those handling the Keith needle would possibly welcome a tool for implanting a penile prosthetic that reduces or eliminates exposure to the sharp end of the Keith needle.

Embodiments provide a tool for measuring a length of the penis distally (forward toward the glans) and proximally (rearward toward the crus) to determine a suitable length for the implantable prosthetics.

Embodiments provide a tool having fewer components than a Furlow introducer. The tool disclosed below omits the plunger employed with the Furlow introducer, yet it retains the function of the Furlow plunger by providing a capability to eject a needle from the tool through the glans penis.

Embodiments provide a tool with fewer components than the Furlow introducer, and yet the tool provides additional functionality over the Furlow introducer. Specifically, the tool has tow sutures attached between a needle and a prosthetic that operate to eject the needle forward through tissue and a separate second suture attached to the needle that operates to retrieve the needle backward into a bore of the tool. Retraction of the needle into the bore of the tool could potentially reduce exposure of the staff to the sharp end of the Keith needle.

Embodiments provide a tool with a first opening (a longitudinal bore) in a distal end and a second opening formed through a wall of the tool to communicate with the bore, where the second opening provides an exit point from the tool for a second suture attached to the needle, where the second suture is employed to retrieve the needle backward into the bore of the tool.

Embodiments provide a needle and a portion of a suture inserted into a bore of a tool. Locating a segment of the suture alongside the needle and distal of a proximal end of the needle advantageously stabilizes the needle before, during, and after the needle is ejected out of the bore. In addition, packing some of the suture alongside the needle within the bore of the tool reduces or eliminates the possibility of the needle undesirably falling away from the tool. Needles that fall out of the tool can become non-sterile if the needle leaves the sterile field and can possibly lead to an increased risk of undesired needle sticks.

Embodiments provide a needle having two eyelets, one toward a proximal end and one toward a distal end of the needle. The two eyelets advantageously stabilize the needle as it is moved longitudinally out of the tool.

Embodiments provide a suture slide formed in a tool proximal (behind) the distal (forward) end of the tool and in front of (distal) a second eyelet formed in the proximal end portion of the needle.

Embodiments provide a suture slide formed as an opening in a wall of a tool somewhere between the proximal end and the distal end of the tool, which provides the advantage of reducing the drag of the suture as it is pulled out of the tool to advance the needle longitudinally out of the tool.

Locating a segment of the suture alongside an entire length of the needle from a proximal end to a distal end of the needle advantageously ensures that the needle remains inserted in the bore during the surgical procedure until the surgeon ejects the needle out of the bore of the tool. Placing the suture alongside the needle and extending the suture out of the opening in the distal end of the tube advantageously ensures that the needle is directed in a linear and controlled fashion out of the tool.

FIG. 1 is a perspective view of one embodiment of a system 20 for implanting an implantable penile prosthetic. The system 20 includes a tool 22 and a suture 24 attached to a needle 26, with the suture 24 looped through a penile prosthetic 28.

The tool 22 includes a bore 30 formed in a tube 32, where the tube 32 is sized for insertion into a dilated corpora cavernosum of the penis.

The suture 24 is passed through an eyelet 40 formed in a proximal end portion of the needle 26 and looped through an eyelet 42 formed in the penile prosthetic 28. In one embodiment, the suture 24 is provided as a single strand 44 including one portion 46 of the single strand 44 passed through the eyelet 42 of the penile prosthetic 28 and two portions 46, 48 of the single strand 44 both and passed through the eyelet 40 of the suture 26. The two portions 46, 48 of the single strand 44 and the needle 26 are inserted into the bore 30. The suture 24 is employed as described below to eject the needle 26 out of the bore 30, through the glans penis, and to subsequently tow the penile prosthetic 28 into the dilated corpora cavernosum. The suture 24 is pulled out of and away from the penile prosthetic 28 after insertion into the corpora cavernosum.

Figure 2:
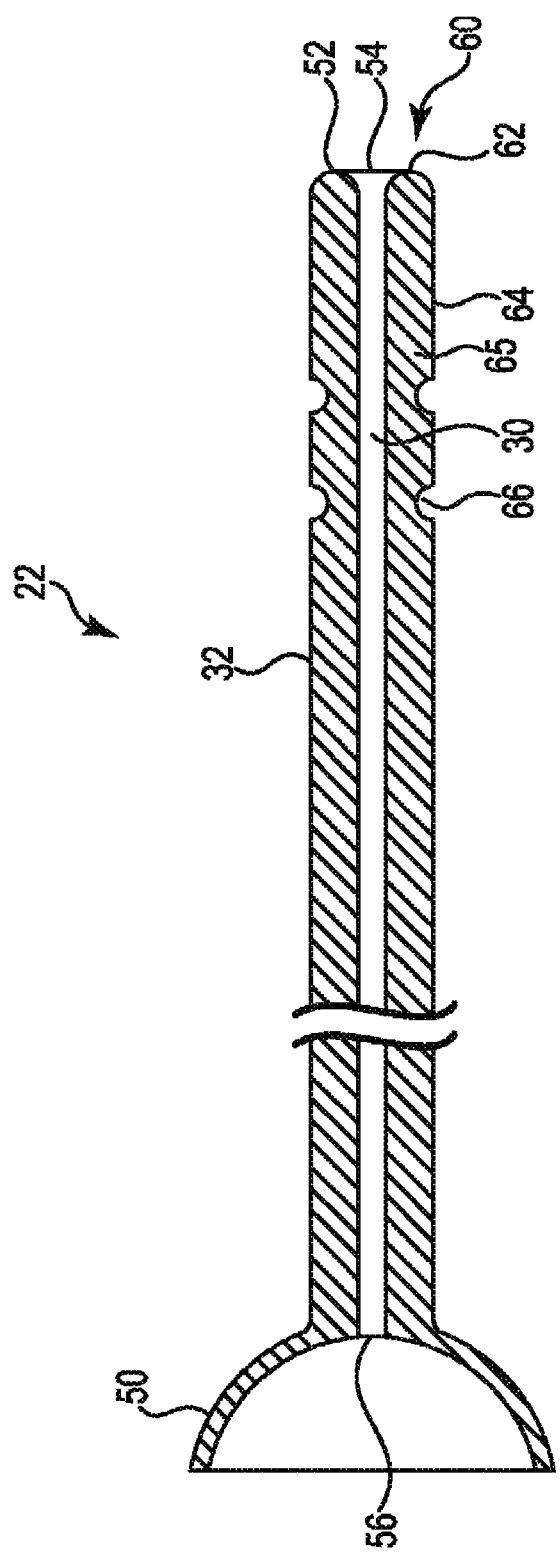
FIG. 2 is a side cross-sectional view of one embodiment of the tool illustrated in FIG. 1.

FIG. 2 is a side or lateral cross-sectional view taken top-to-bottom through the tool 22. The tube 32 extends between a handle portion 50 on one end and a distal end 52. The bore 30 is formed in the tube 32 and extends between a first opening 54 at the distal end 52 and a second opening 56 that is located proximal of the distal end 52 of the tube 32. The tube 32 is provided with a suture slide 60 that is configured to allow the suture 24 (FIG. 1) to be pulled out of the bore 30 of the tool 22.

In one embodiment, the suture slide 60 is monolithically integrated as a part of a wall of the tube 32, which provides the advantage of a smooth instrument for insertion into a dilated corpora cavernosum.

Suitable tubes for the tool 22 are described below and include various embodiments of suture slides.

In one embodiment, the suture slide 60 is located at the distal end 52 of the tube 32 and includes a curved surface 62 formed between an exterior surface 64 of the tube 32 and the bore 30. In the embodiment of FIG. 2, the tube 32 has a tube wall 65 extending continuously between the handle portion 50 and the distal end 52, where the tube 32 is characterized by an absence of a slot or other opening formed in the tube wall 65. As noted in FIG. 1, the two portions 46, 48 of the suture 24 are inserted into the bore 30 along with the needle 26. The bore 30 can become crowded by the two portions 46, 48 of the suture 24 and the needle 26. One advantage of forming the tube 32 to have an absence of a slot or opening formed into the tube wall 65 is to ensure that the suture 24 and the needle 26 inserted in the bore 30 are both captured securely in a manner that resists their falling out of the bore 30 during a surgical procedure. One advantage of the curved surface 62 of the suture slide 60 is to provide reduced resistance to the suture 24 as the suture 24 and the needle 26 are ejected out of the crowded bore 30 of the tube 32.

The tube 32 is sized for insertion into one of the two corpora cavernosa of the penis. A suitable diameter for the tube 32 is in a range from 0.5-3.0 centimeters, and preferably the diameter of the tube 32 is in a range from about 0.7-2 centimeters. A suitable inside diameter for the bore 30 is in a range from 0.5 mm-4.0 mm, and preferably the inside diameter of the bore 30 is in a range from about 1 mm-3 mm. In one embodiment, one or more marks 66 is/are formed in the exterior surface 64 of the tube. One advantage of the mark 66 is to provide an indication of a measured distance away from the distal end 52 of the tube 32, which is useful when measuring the depth of the corpora cavernosum. In one embodiment, a series of the marks 66 are provided to measure distances (e.g., 12 cm, 14 cm, 16 cm, etc.) away from the distal end 52 of the tube 32.

The handle portion 50 of the tool 22 allows the surgeon to control the tube 32 while maintaining access to the corpora cavernosa. In one embodiment, the handle portion 50 is funnel-shaped with the second opening 56 located at the bottom of the funnel-shape. Other suitable shapes for the handle portion 50 are also acceptable, including handles with a finger grooves, a T-shaped handle, or an L-shaped handle.

The tool 22 is suitably fabricated from plastic or metal. With additional reference to FIG. 1, it is beneficial to provide the suture 24 and the needle 26 pre-loaded into the tool 22 for each predetermined length (12 cm, 14 cm, 16 cm, etc.) of penile prosthetic. With this in mind, it is beneficial to provide the tool 22 in a disposable (plastic or metal) format. Reusable, for example stainless steel, tools 22 are also acceptable.

Figure 3:
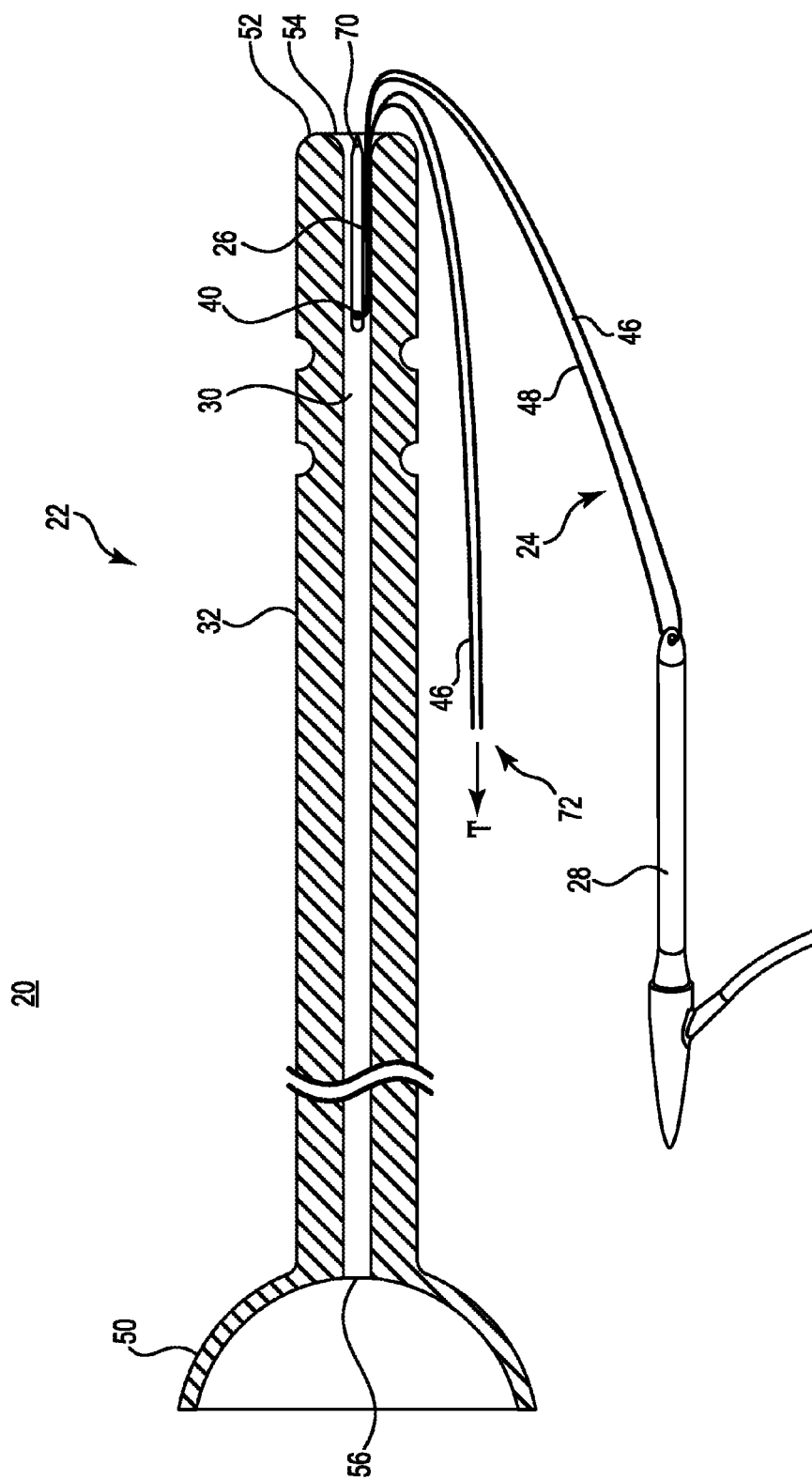
FIG. 3 is a top cross-sectional of the tool illustrated in FIG. 2.
Figure 4:
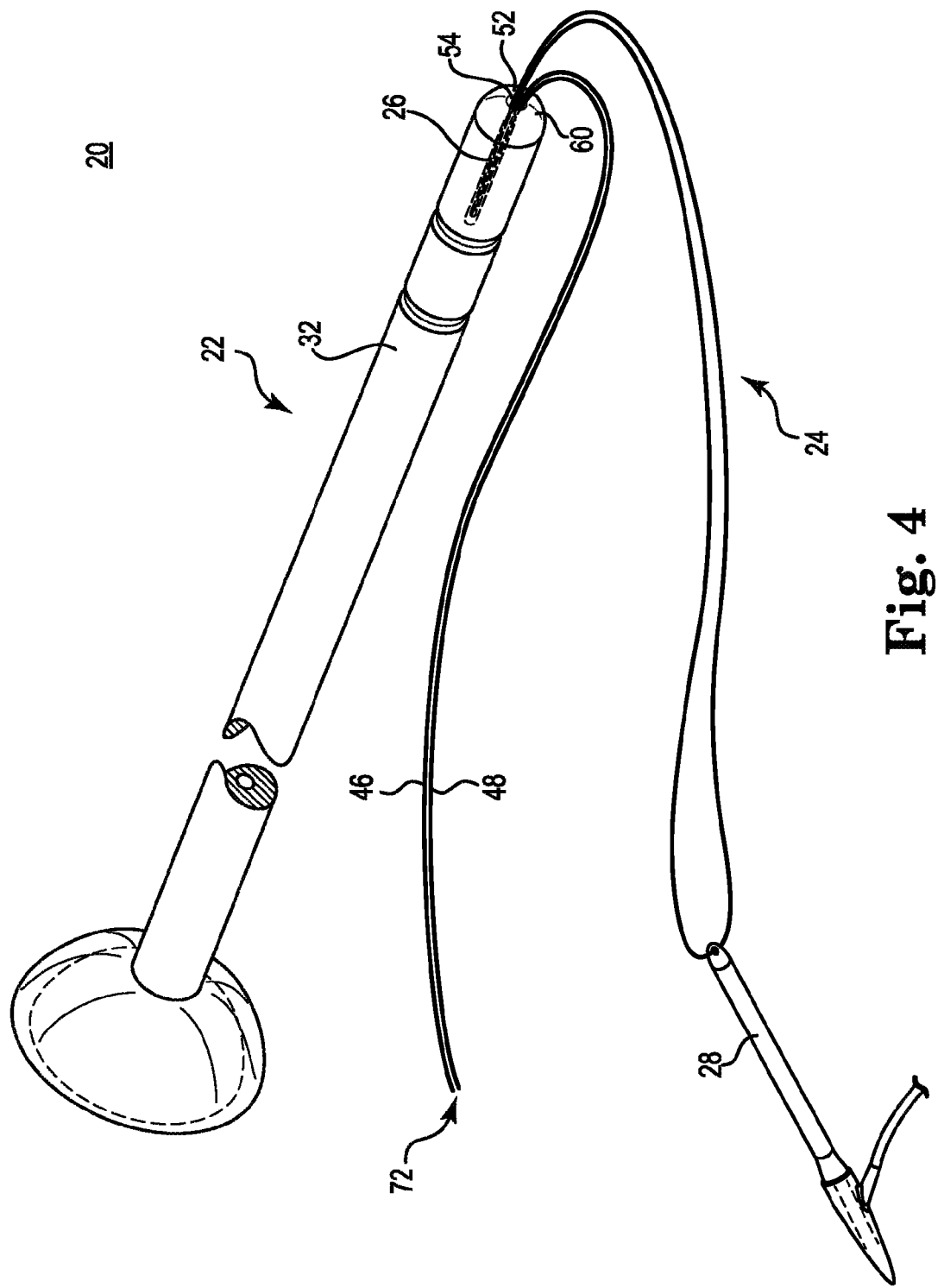
FIG. 4 is a perspective view of the system illustrated in FIG. 1 with the needle and a segment of suture inserted into the tool.

FIG. 3 is a cross-sectional view and FIG. 4 is a perspective view of the system 20 assembled as it would be supplied in a kit of parts for implantation of the penile prosthetic 28 into a penis. The two portions 46, 48 of the suture 24 are looped through the eyelet 40 formed in the proximal end portion of the needle 26. The needle 26 is inserted in the bore 30 with a pointed distal end 70 of the needle 26 closer to the first opening 54 than it is to the second opening 56. The portions 46, 48 of the suture 24 are also inserted within the bore 30 and are placed alongside (parallel to) the needle 26. The eyelet 40 part of the needle 26 is behind (or rearward or proximal) to the suture slide 60 where the suture 24 exits the bore 30. In one embodiment, the needle 26 and the portions 46, 48 are packed into the bore 30 in a friction-fit manner that prevents the needle 26 from falling out of the bore 30 under the weight of gravity. One advantage of packing some of the suture 24 alongside the needle 26 within the bore 30 is that the possibility of the needle 26 undesirably falling out of the bore 30 is reduced or eliminated.

FIG. 4 illustrates the system 20 as assembled. The system 20 uses the suture slide 60 as a pulley to transfer the rearward, proximal force applied to the free end 72 of the suture 24 into movement of the needle 26 out of the bore 30 in the distal direction. The system 20 operates to trade force (applied to the free ends 72) for distance (movement of the needle 26 in the distal direction) in a manner similar to the operation of a pulley. The tool 22 is configured to allow the needle 26 to exit the bore 30 only when a sufficient force is applied to the suture 24 to pull the needle 26 out of the tool 22.

The system 20 is characterized by an absence of a plunger or obturator device inserted into the second opening 56 of the bore 30. Two advantages of omitting a plunger from the system 20 is a reduction in the number of parts and ease of use for the surgeon.

The suture 24 extends out of the first opening 54, contacts the suture slide 60, and extends to a pair of free ends 72. The suture 24 is tensioned when a force is applied to pull the free ends 72 of the suture 24 away from the distal end 52 of the tool 22, which causes a portion of the suture 24 to move over the suture slide 60. The tension in the suture 24 and the movement of the suture 24 on the suture slide 60 pulls the proximal end portion of the needle 26 forward in a distal direction. The pulling force applied to the needle 26 by the suture 24 ejects the needle 26 in the distal direction out of the bore 30 of the tool 22. The suture slide 60 is provided to reduce the resistance of the suture 24 as it exits from the bore 30 of the tool 22.

Figure 5:
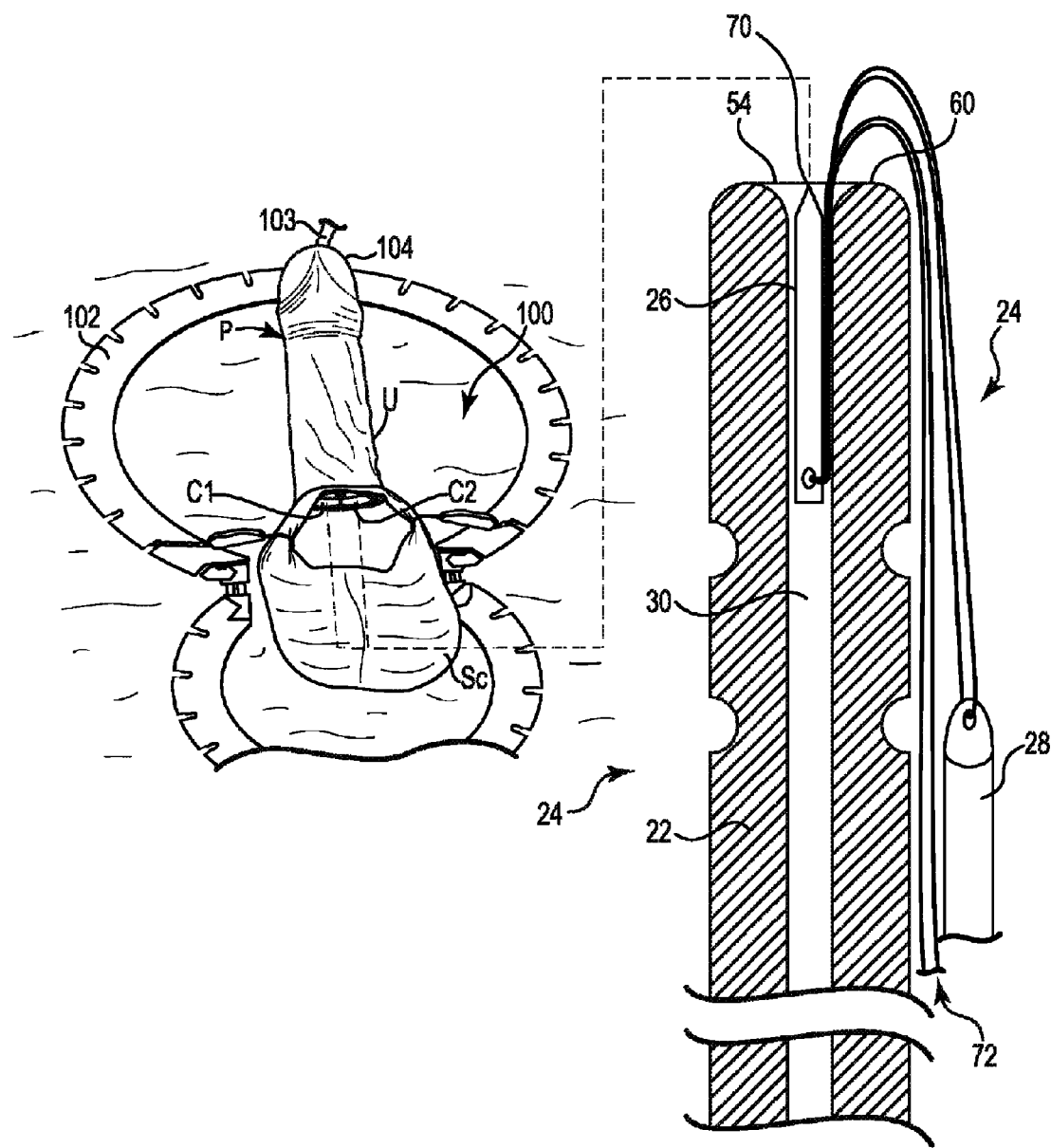
FIG. 5 is a cross-sectional view of the system illustrated in FIG. 4 during implantation of a penile prosthetic.
Figure 6:
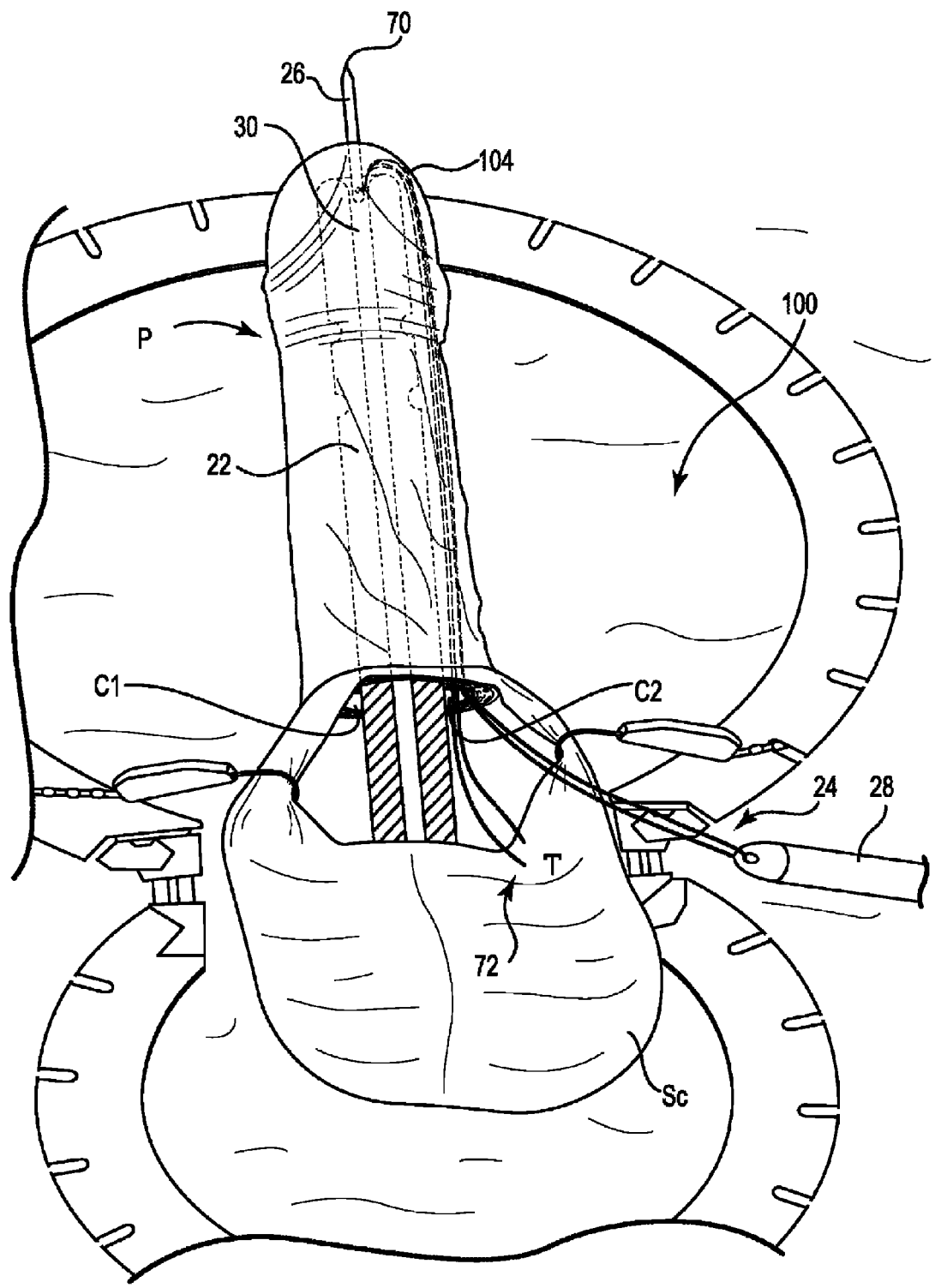
FIG. 6 is a cross-sectional view of the system illustrated in FIG. 5 with the needle ejected out of the bore of the tool.

FIG. 5 and FIG. 6 are schematic cross-sectional views of the system 20 employed to implant a penile prosthetic 28 into a penis P.

The penis P is reclined against the torso and incised to expose the corpora cavernosa (C1 and C2).

The groin area 100 of the patient is shaved, cleaned and suitably prepped with a surgical solution prior to draping with a sterile drape as directed by the healthcare provider's procedures. A retraction device, such as those available from Lone Star Medical Products of Stafford, Tex., is placed around the penis P if so desired by the surgeon to establish the surgical field. A catheter 103 is inserted into the urethra U from the distal end 104 of the penis P. Thereafter, the surgeon forms an incision to access the corpora cavernosa C1 and C2 of the penis.

Suitable examples of incisions include either an infrapubic incision or a transverse scrotal incision. The infrapubic incision is initiated between the umbilicus and the penis (i.e., above the penis), whereas the transverse scrotal incision is made across an upper portion of the patient's scrotum Sc.

As an example of the transverse scrotal approach, the surgeon forms a 2-3 cm transverse incision through the subcutaneous tissue of the median raphe of the upper scrotum Sc and dissects down through the Darto's fascia and Buck's fascia to expose the tunicae albuginea of the penis P. Thereafter, each corpora cavernosum C1 and C2 is exposed in a corporotomy where a small (approximately 1.5 cm) incision is formed to allow the surgeon to access and subsequently dilate the corpora cavernosa C1 and C2.

The surgeon typically will insert a blunt-ended scissors or other elongated tool to separate a portion of the spongiosum material to open a pathway for dilation and measurement of the corpora cavernosum C1, C2. After suitable dilation, the surgeon measures the length of the corpora cavernosa to determine the suitable size for the penile prosthetic 28. In one approach, the surgeon ensures that the appropriately sized penile prosthetic 28 has been selected by inserting the tool 22 into the corpora cavernosa C1 or C2 and using the marks 66 to measure the proximal and distal length of each corpora cavernosum C1 and C2. For example, the tool 22 is inserted into one of the corpora cavernosa C1 or C2 forward in the distal penis toward the glans penis, the distal measurement is recorded by reading one of the marks 66, and the tool 22 is inserted into the same corpora cavernosa C1 or C2 rearward in the proximal penis toward the crus of the penis to record the proximal length of the corpora by reading one of the marks 66. The distal and proximal measurements would typically be made in reference to a "stay stitch" temporarily placed in the incision. The sum of the distal and the proximal measurements represent the length of that corpora cavernosum, and this information is compared to the selected size of the penile prosthetic 28. This procedure is repeated for the other of the corpora cavernosa C1 or C2 to ensure the appropriately sized penile prosthetic 28 has been selected for the companion corpora.

FIG. 5 illustrates the penis P prepped for surgery and the system 20 prepared for implantation of the penile prosthetic 28 into the corpora cavernosum C2. The needle 26 is retained within the bore 30 with the pointed distal end 70 of the needle rearward (proximal) of the first opening 54. A portion of the suture 24 is disposed alongside the needle 26 and extends to a location that is distal of both the proximal end and the pointed distal end 70 of the needle 26.

FIG. 6 is a schematic view of the tool 22 inserted into the corpora cavernosum C2. The free ends 72 of the suture 24 are outside of the penis P and available to the surgeon. The penile prosthetic 28 is outside of the penis P, attached to the suture 24. The surgeon, through experience, applies sufficient tension to the free ends 72 of the suture 24 to eject the needle 26 forward out of the glans penis. The proximal, rearward force applied to the free ends 72 of the suture 24 is transferred in a pulley-like fashion to drive the needle 26 is a distal direction. The surgeon employs a forceps or other tool to grasp the needle 26. The needle 26 is held stationary outside of the penis P as the tool 22 is removed from corpora cavernosum C2. Thereafter, the needle 26 is snipped from the suture 24, and the remaining suture 24 is employed to tow the penile prosthetic 28 distally into the corpora cavernosum C2 up to the glans penis. The suture 24 is removed from the prosthetic 28.

The proximal end of the penile prosthetic 28 is suitably implanted proximately into the crus penis.

A second penile prosthetic is implanted in the corpora cavernosum C1 following the steps described above for implantation of the penile prosthetic 28 the corpora cavernosum C2.

Figure 7:
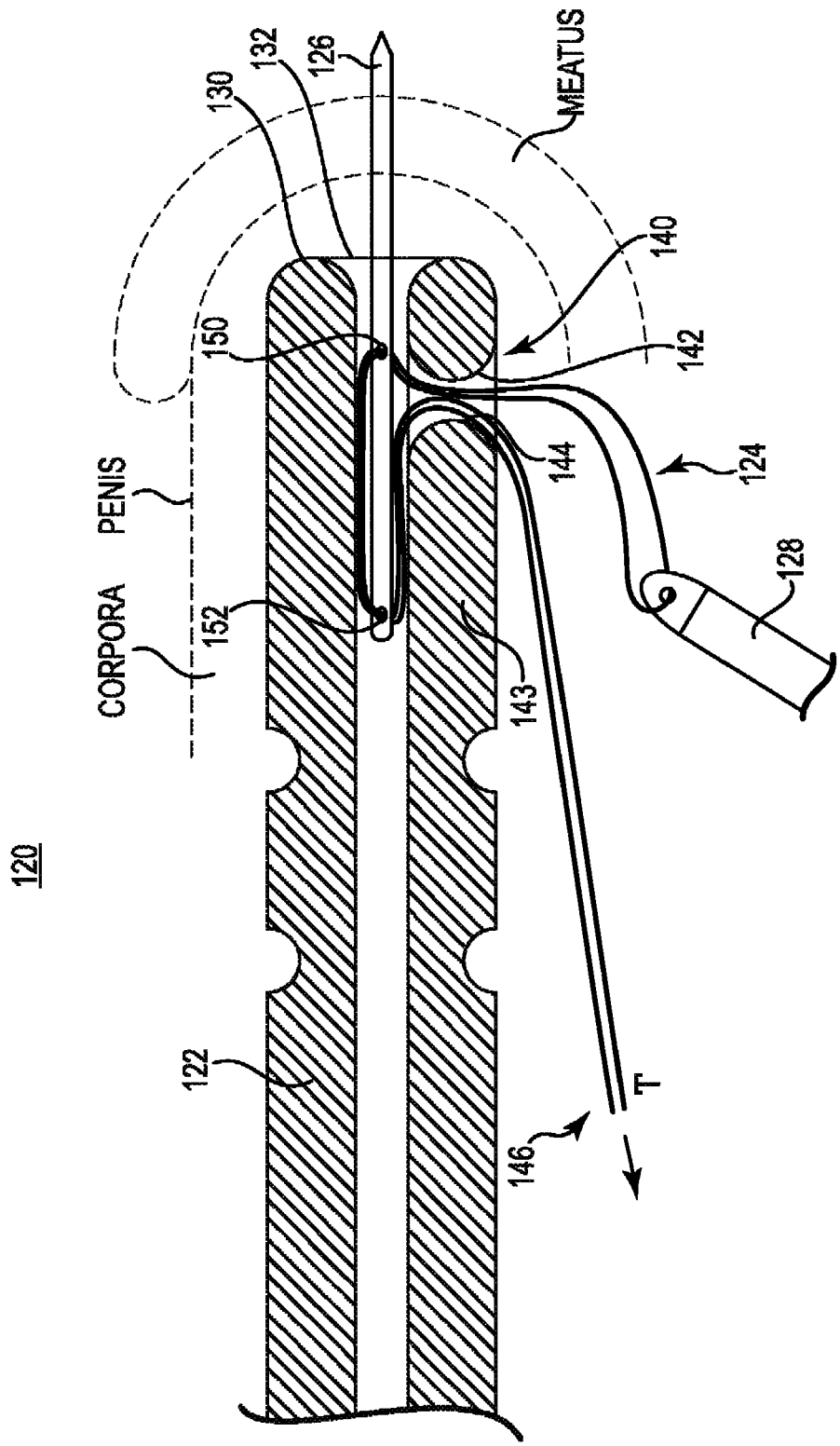
FIG. 7 is a side cross-sectional view of one embodiment of a system for implanting an implantable penile prosthetic.

FIG. 7 is a cross-sectional view of one embodiment of a system 120 configured for implanting an implantable penile prosthetic 128 into a penis. The system 120 includes a tool 122 and a suture 124 engaged between a needle 126 and the penile prosthetic 128.

The tool 122 includes an annular tube extending between a handle portion (not illustrated in FIG. 7 since the handle portion is similar to the handle portion illustrated in FIG. 2) and a distal end 130 that is provided with a first opening 132. One embodiment of the tool 122 includes a suture slide 140 that is located proximal (behind) the distal end 130 of the tool 122 and in front of (distal) the second eyelet 152 formed in the proximal end portion of the needle 126. In one embodiment, the suture slide 140 is provided as an opening 141 formed in a tube wall 143 of the tool 122 and includes a first surface 142 and a second surface 144. The suture 124 located between the prosthetic 128 and the needle 126 slides along the first surface 142, and the suture 124 between the needle 126 and the free ends 146 slides along the second surface 144. In one embodiment, at least the second surface 144 is provided with a curved surface that reduces resistance of the suture 124 as it is pulled out of the tool 122. In one embodiment, each of the first surface 142 and the second surface 144 is provided as a curved surface.

Locating the suture slide 140 between the proximal end (rear end) of the needle 126 and the distal end 130 of the tool 122 configures the system such that tension T applied to the free ends 146 of the suture 124 will eject the needle 126 in a distal direction through the meatus of the penis. Advantages of providing the suture slide 140 as an opening 141 formed in the tube wall 143 include a neatly designed system that is pleasant to use and reducing or eliminating binding of the suture 124 when tension T is applied to the suture 124 to eject the needle 126 out of the first opening 132. As noted above, the bore of the tool 122 can become crowded after inserting both the suture and the needle into the bore. Providing the suture slide 140 as a separate opening formed in the wall 143 of the tool 122 advantageously reduces the binding of the suture 124 as it exits the tool 122.

In one embodiment, the needle 126 includes a first eyelet 150 and a second eyelet 152. At least the second eyelet 152 is located on a proximal end portion of the needle 126. The suture 124 is threaded through the eyelet of the penile prosthetic 128, extends over the first surface 142 of the suture slide 140, engages the needle 126 through the first eyelet 150, extends alongside the needle 126 to the second eyelet 152, exits the second eyelet 152, extends around the second surface 144 of the suture slide 140, and terminates in the free ends 146. One advantage of employing two eyelets 150, 152 is to reduce the pitch (up-and-down movement) and the yaw (side-to-side movement) of the needle 126 as it exits the first opening 132.

The needle 126 and the suture 124 are inserted in the bore of the tool 122 and combine to occupy a volume of space. One advantage of locating the suture slide 140 between the proximal end portion of the needle 126 and the distal end 130 of the tool 122 is to provide clearance for the suture 124 entering and exiting the tool 122. The clearance ensures that the needle 126 is controlled as it is ejected as a result of the tension applied to the free ends 146 of the suture 124.

FIG. 8-FIG. 11 are cross-sectional views of one embodiment of a system 200 configured for implanting an implantable penile prosthetic.

Figure 8:
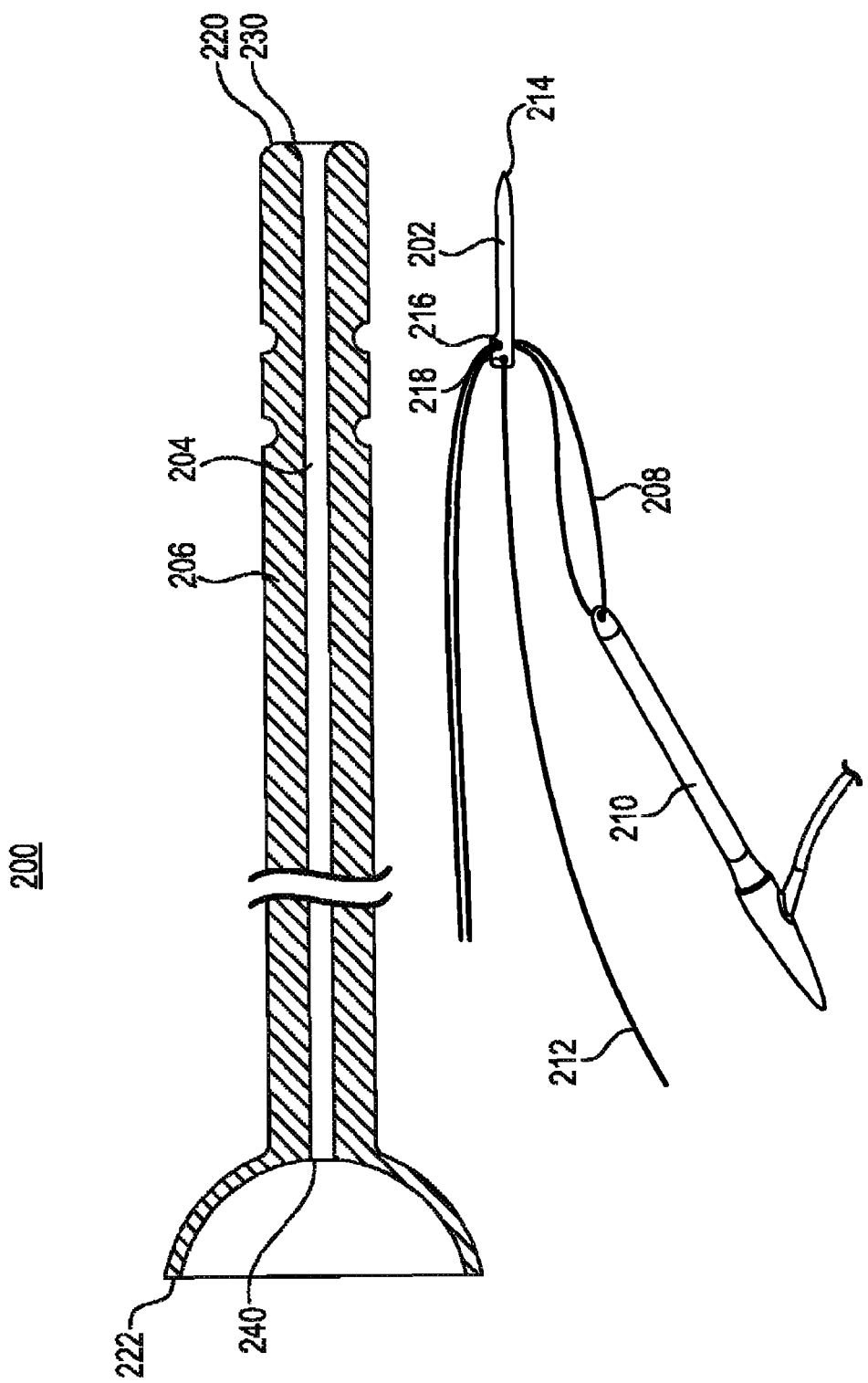
FIG. 8 is a cross-sectional view of one embodiment of a system with two sutures useful for implanting an implantable penile prosthetic.

FIG. 8 is a cross-sectional view of a tool 206 of the system 200. The system 200 includes a needle 202 that is insertable into a bore 204 of the tool 206, a first suture 208 engaged between the needle 202 and a penile prosthetic 210, and a second suture 212 connected to the needle 202.

The needle 202 includes a pointed distal end 214 and a proximal end portion 216. The first suture 208 is engaged with the proximal end portion 216 of the needle 202 and the second suture 212 extends from a distal end 218 of the needle 202.

The tool 206 extends between a distal end 220 and a proximal end 222. A first opening 230 is formed in the distal end 220, and a second opening 240 is formed in the proximal end portion of the tool 206.

Figure 9:
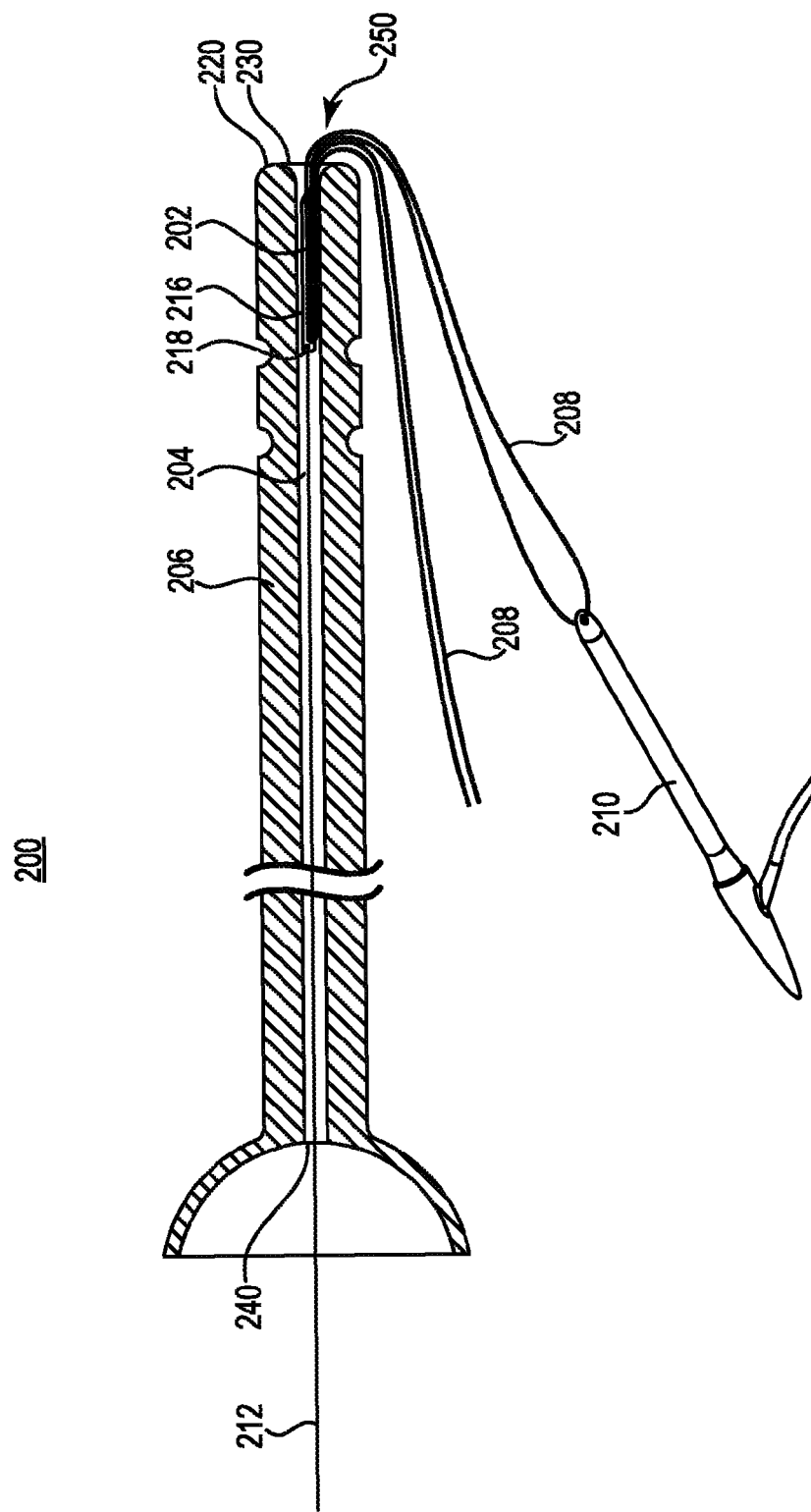
FIG. 9 is a cross-sectional view of the system illustrated in FIG. 8 including a first suture coupled between a penile prosthetic and a needle and a second suture extending away from the needle.

FIG. 9 is a cross-sectional view of the needle 202 placed within the bore 204 of the tool 206. The first suture 208 is attached to the proximal end portion 216 of the needle 202, extends alongside the needle 202, and exits the first opening 230 formed in the distal end 220 of the tool 206. In one embodiment, a suture slide 250 is formed as a curved wall located at the distal end 220 of the tool 206. The first suture 208 extends from the needle 202 over the suture slide 250. The second suture 212 is attached to the proximal end 218 of the needle 202, extends along the bore 204 of the tool 206, and exits the tool 206 through the second opening 240. One alternative embodiment includes forming the suture slide 250 as an opening in a wall of the tool 206 as in FIG. 7, with the alternative suture slide located proximal or behind the distal end 220 of the tool 206.

FIG. 10 illustrates tension applied to the first suture 208 to pull the proximal end portion 216 of the needle 202 in a distal direction, which ejects the needle 202 out of the first opening 230. The second suture 212 is attached to the proximal end 218 of the needle 202 and moves within the bore 204. The needle 202 is movable in a distal direction in response to tension applied to the first suture 208, which operates to push the needle 202 out of the first opening 230 of the tool 206 through the meatus of the penis (see FIG. 7).

The surgeon tows the penile prosthetic 210 into one of the corpora cavernosum by pulling on the first suture 208. The first suture 208 is subsequently severed and pulled away from the needle 202 and discarded. The needle 202 remains attached to the second suture 212.

FIG. 11 is a cross-sectional view illustrating the second suture 212 employed to retract the needle 202 back into the bore 204 of the tool 206. Tension is applied to the second suture 212 to pull the needle 202 backwards in a proximal direction, which returns the needle 202 back into the bore 204 of the tool 206. The needle 202 is now stowed inside the tool 206. The tool 206 and the needle 202 are removed from the corpora cavernosum and discarded.

Figure 12:
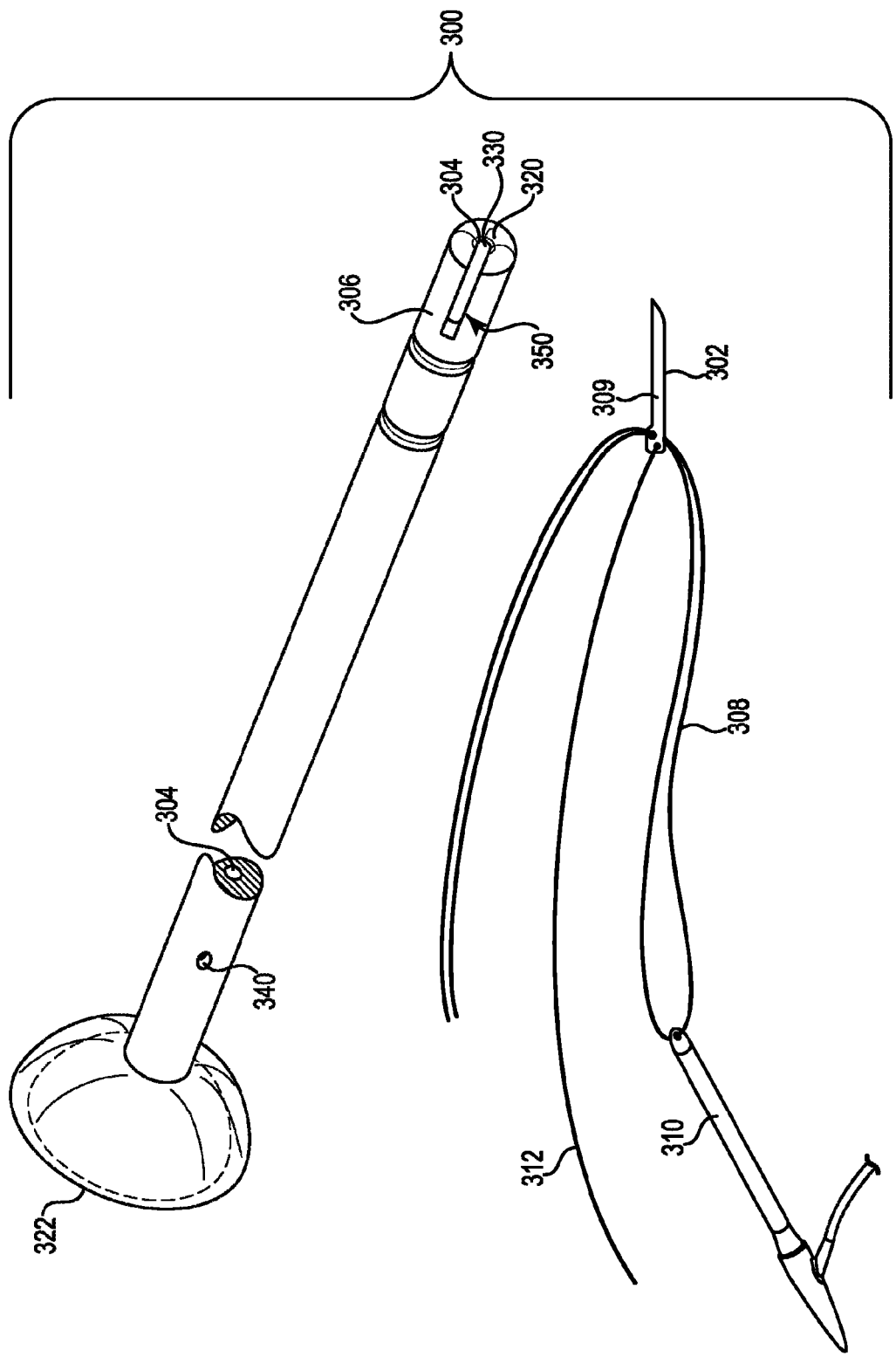
FIG. 12 is a perspective view of one embodiment of a system for implanting an implantable penile prosthetic.
Figure 13:
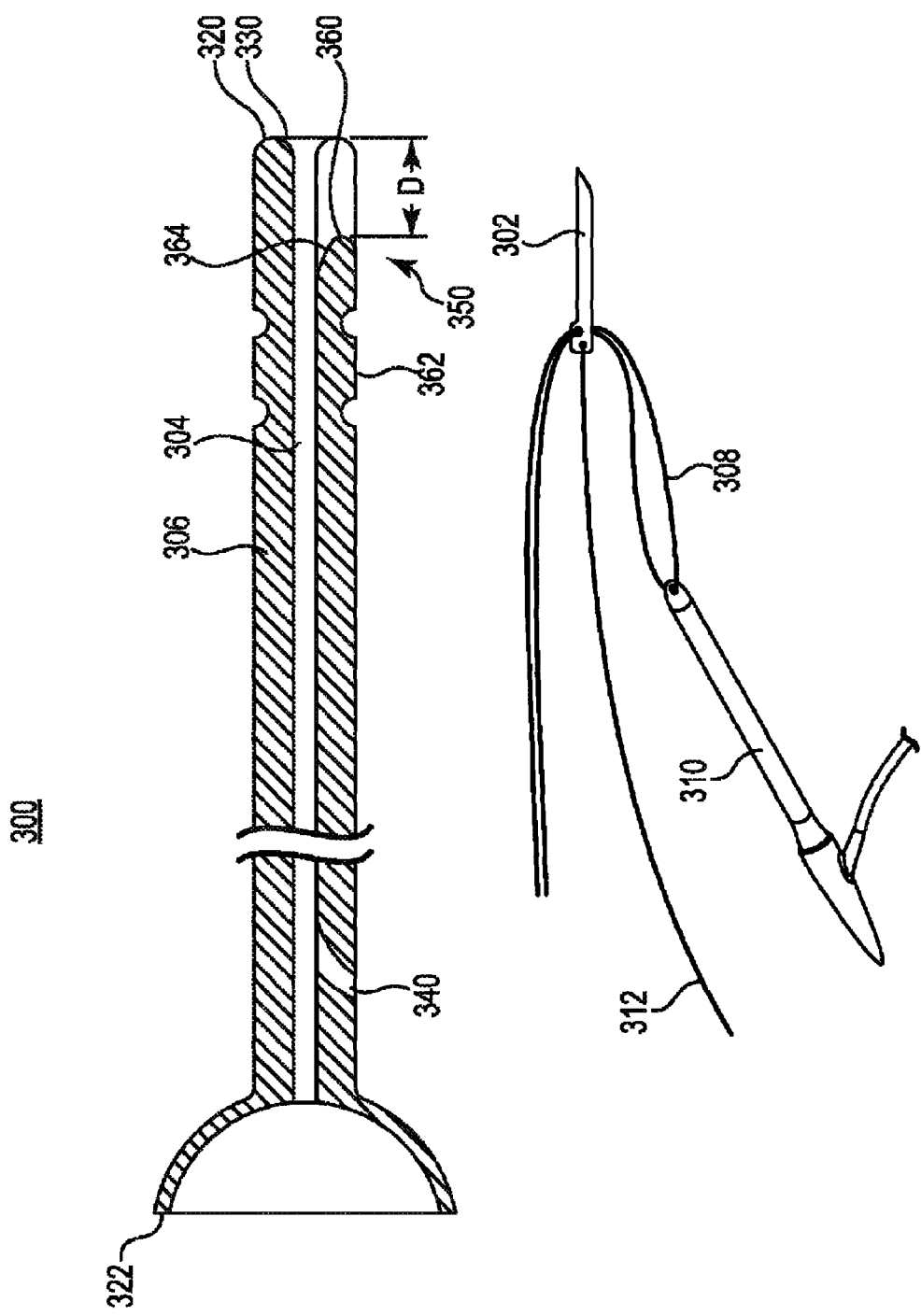
FIG. 13 is a cross-sectional view of the tool of the system illustrated in FIG. 12.
Figure 14:
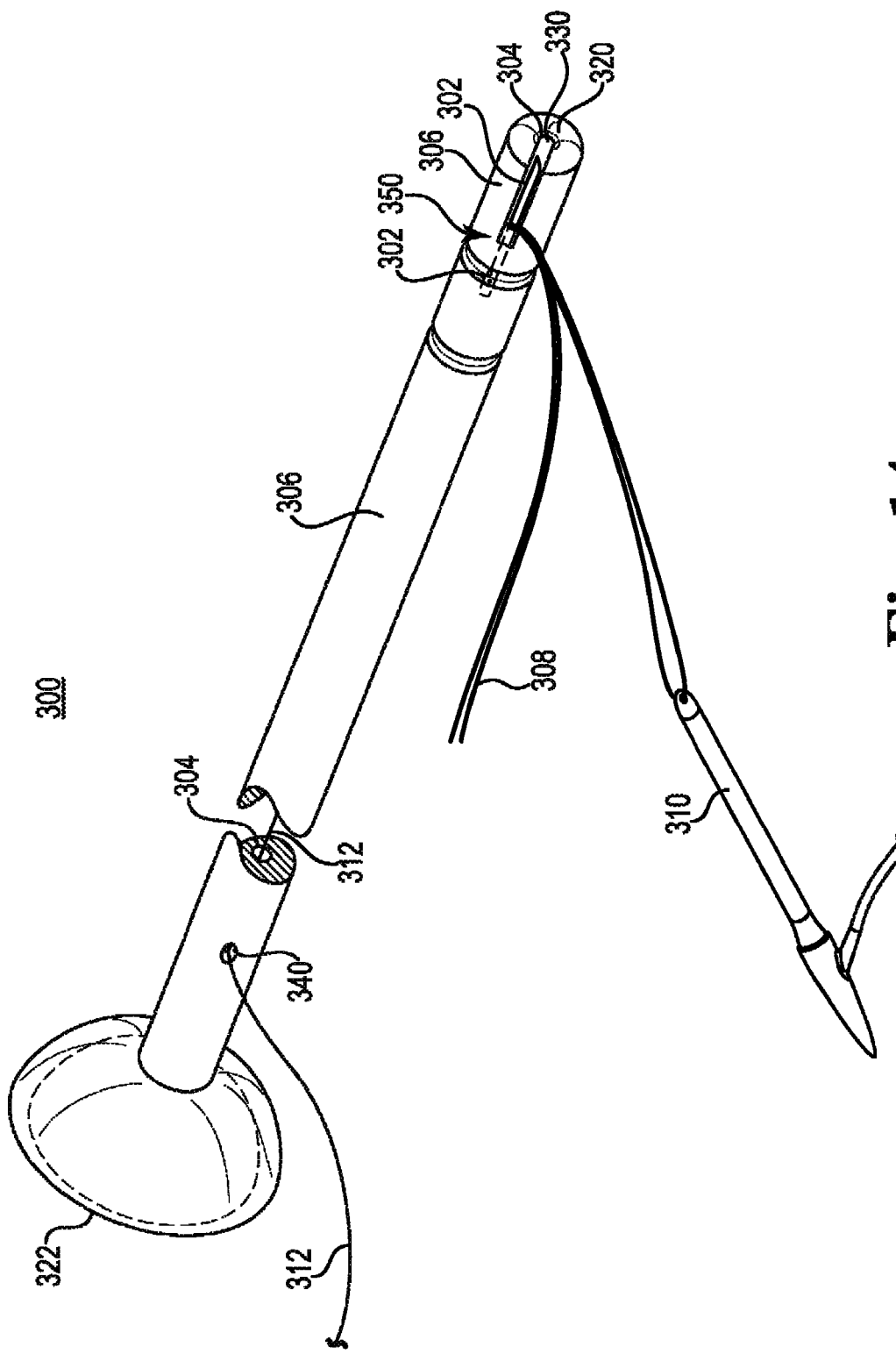
FIG. 14 is a perspective view of the system illustrated in FIG. 12 with a needle inserted into the tool and prepared for implantation of an implantable penile prosthetic.

FIG. 12, FIG. 13, and FIG. 14 illustrate embodiments of a system 300 for implanting an implantable penile prosthetic 310 having a suture slide 350 that is not located at the distal end of a tool 306. With reference to FIG. 9, the multiple strands of suture attached to the needle and to the implant can begin to accumulate near the distal end of the tool. Locating the suture between the proximal end portion of the needle inserted in the bore and the distal end of the bore provides clearance for the suture strand, which advantageously provides relief between the system 300 and the tissue.

FIG. 12 is a perspective view of the system 300. The system 300 includes a needle 302 insertable into a bore 304 of a tool 306, a first suture 308 secured between a proximal end portion 309 of the needle 302 and the penile prosthetic 310, and a second suture 312 connected to the needle 302. When the system 300 is assembled, the needle 302 and the sutures 308, 312 are located in the bore 304 of the tool 306.

The tool 306 extends between a distal end 320 and a proximal end 322 that typically includes a handle or other control device. A first opening 330 is provided at the distal end 320, and a second opening 340 is formed through a wall of the tool 306 to communicate with the bore 304. The proximal end 322 of the tool 306 provides a handle that is useful when manipulating the tool 306 to implant the penile prosthetic 310. In one embodiment, a suture slide 350 is formed through the wall of the tool 306 to communicate with the bore 304. The suture slide 350 is formed in a distal end portion of the tool 306 and extends forward to the distal end 320 of the tool 306.

FIG. 13 is a cross-sectional view of the system 300 prior to assembly, and FIG. 14 is a perspective view of the system 300 after assembly.

The suture slide 350 is formed a distance D behind the distal end 320 of the tool 306. In one embodiment, the suture slide 350 is formed by a complex curvature including a first curved surface 360 extending from an exterior 362 of the tool 306 and a second curved surface 364 extending from the first curved surface 360 to the bore 304. In one embodiment, a radius of curvature of the first surface 360 is different from the radius of curvature for the second surface 364. In one embodiment, a radius of curvature for the first surface 360 is smaller than (less than) a radius of curvature for the second surface 364. One advantage of providing the suture slide 350 with a complex curvature is to reduce the drag of the suture along the slide as the suture is tensioned to position/implant the penile prosthetic 310 in the penis.

FIG. 14 illustrates the system 300 assembled with the needle 302 placed into the bore 304, with the first suture 308 extending out of the suture slide 350 and the second suture 312 extending out of the second opening 340. The first suture 308 is disposed alongside of the needle 302 and exits the suture slide 350. The suture slide 350 is in front of (distal) a proximal end of the needle 302 and behind (proximal) the distal end 320 of the tool 306. The suture slide 350 is structured to allow the first suture 308 to exit the bore 304 generally along the second surface 364 prior to curving in a direction that directs the suture 308 towards the proximal end 322 of the tool 306.

In one embodiment, the suture slide 350 is located between the proximal portion of the needle 302 and the distal end 320 of the bore 304, with the suture slide 350 provided as an opening or a slot formed in a wall of the tubular tool 306. In one embodiment, the suture slide 350 is located midway between the proximal portion of the needle 302 and the distal end 320 of the bore 304. Locating the suture slide 350 between the proximal portion of the needle 302 and the distal end 320 of the bore 304 had the advantage of combining a level of frictional engagement to retain the suture/needle within the bore and a level of an ease of extraction when ejecting the needle out of the bore.

The first suture 308 is connected to the needle 302 and the penile prosthetic 310. Pulling on, or applying tension to the first suture 308 pulls the needle 302 out of the first opening 330 of the tool 306. This maneuver allows the needle 302 to be ejected from the bore 304 through the meatus of the penis. The surgeon separates the first suture 308 from the needle 302, and employs the first suture 308 to subsequently tow the penile prosthetic 310 into the corpora cavernosum.

The second suture 312 extends away from the needle 302 and exits the second opening 340 formed in the tool 306. The surgeon pulls on the second suture 312 to return the needle 302 back into the bore 304 of the tool 306, where the needle 302 is safely retained within the tool 306. The second opening 340 is located near where the surgeon would place his or her hands when manipulating the tool 306, and this positions the second suture 312 for convenient manipulation/retraction of the needle 302 back into the tool 306.

One advantage of locating the suture slide 350 behind (proximal) from the distal end 320 of the tool 306 is to ensure improved traction or control of the first suture 308 as the needle 302 is ejected from the bore 304.

One advantage of locating the second opening 340 between the distal end 320 and the proximal end 322 of the tool 306 is to locate the second suture 312 in a natural location for the surgeon to access and manipulate. The second suture 312 is essentially out of the way during implantation procedure for the penile prosthetic 310, and is easily accessed for retracting the needle 302 back in the bore 304.

In one embodiment, the system 300 is assembled as illustrated in FIG. 14 during the manufacturing process, packaged with instructions on its use, and inventoried for shipment to end users as a ready to use system.

Figure 15:
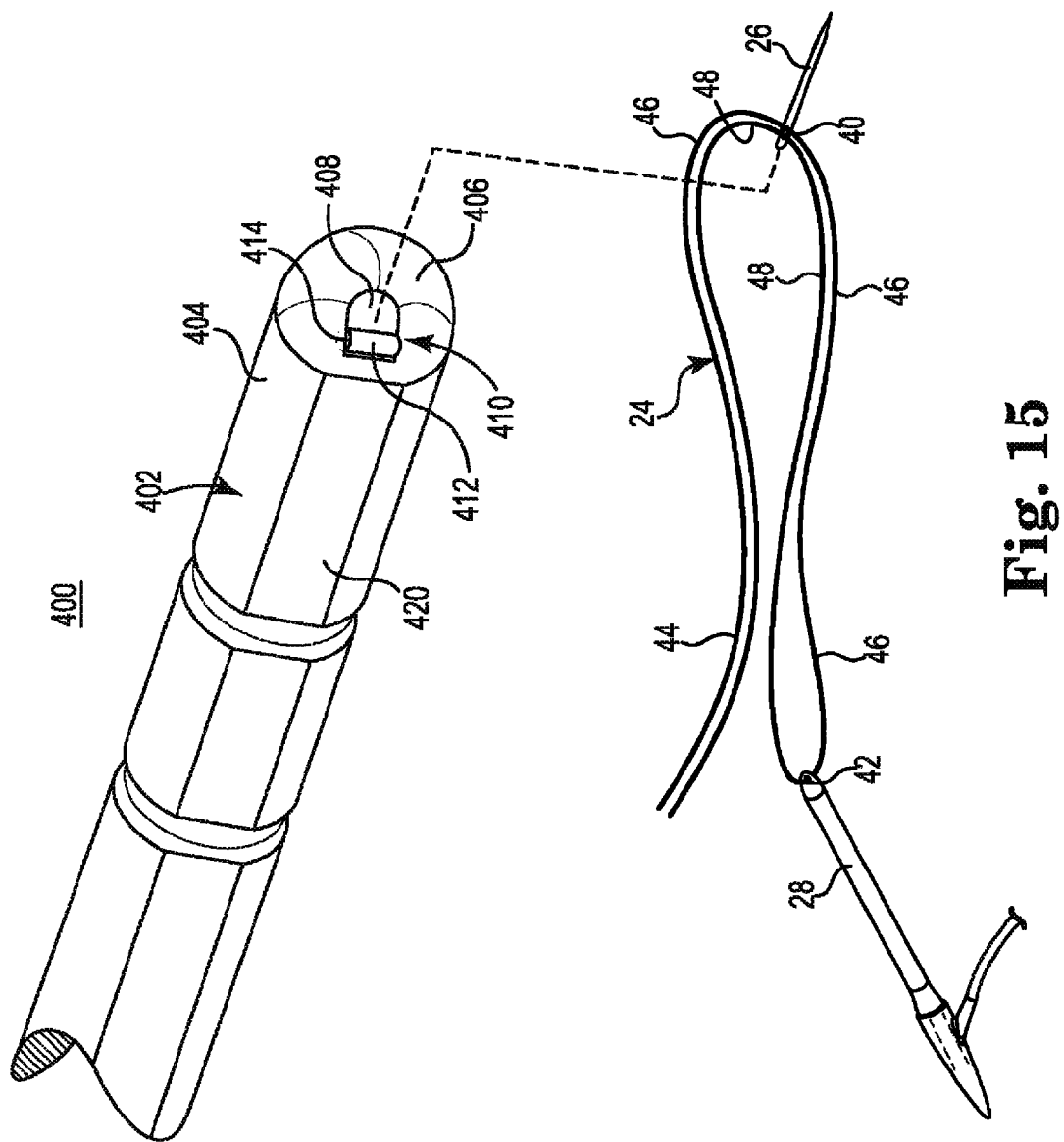
FIG. 15 is a perspective view of one embodiment of a system for implanting an implantable penile prosthetic including a needle and a tool.

FIG. 15 is a perspective view of one embodiment of a system 400 including the penile prosthetic 28 associated with the needle 26. The system 400 includes a tool 402 having a tube 404 extending to a distal end 406, with a bore 408 formed in the tube 404. As described above, the needle 26 and some of the suture 24 are inserted into the bore 408 for delivery of the prosthetic 28 into the corpora cavernosum. A suture slide 410 is located at the distal end 406 of the tube 404 to facilitate dispensing the suture 24 out of the bore 408. In one embodiment, the suture slide 410 is a rotatable conveyance bar attached to the tube 404 and operates to convey the suture 14 out of the bore 408 during implantation of the prosthetic 28, similar to the procedures described above for other embodiments of the tools.

The suture slide 410 operates in a pulley-like manner to transfer the force applied to the suture 24 into forward motion of the needle 26. In one embodiment, the suture slide 410 is a cylinder 412 that is attached to the tube 404 by an axel 414, which allows the cylinder 412 to rotate on its axis as the suture 24 is pulled out of the bore 408. Clearance between the tool 402 and the tissue can be limited when the tube 404 is inserted into the dilated corpora cavernosum, and the reduced clearance can impart a high level of drag onto the suture 24 as the suture 24 is pulled to deploy the needle 26. The rotation of the cylinder 412 advantageously contributes to reducing the friction of the suture 24 as it is withdrawn from the bore 408 during implantation of the prosthetic 28.

The surgeon will find it useful to locate or identify the position of the suture slide 410 when the tool 402 is inserted into the corpora cavernosum, which would ordinarily block the view of the suture slide 410. In one embodiment, a guide 420 is formed in an exterior surface of the tube 404, where the guide 420 is co-located with (aligned longitudinally with) the suture slide 410 to provide a visual indicator of the location of the suture slide 410. The guide 420 is suitably provided as a visual marking, such as a colored line, or a physical marking such as a flat surface formed in the tube 404. The surgeon is able to view that portion of the tube 404 that extends out of the corpora cavernosum (see FIG. 6) to see the guide 420, which identifies the location of the suture slide 410. The suture 24 is pulled along the side of the tool 402 where the suture slide 410 is located.

A single suture slide 410 is illustrated in FIG. 15, although it is acceptable to provide the distal end 406 of the tool 402 with multiple rotating suture slides placed side-by-side around the bore 408. Several small suture slides, similar to suture slide 410, may be attached around a perimeter of the bore 408 to provide the entire perimeter of the bore 408 with a rotating suture slide. Alternatively, two or three or more suture slides may be placed around the bore 408.

Although specific embodiments have been illustrated and described, it will be appreciated by those of ordinary skill in the art that a variety of alternate and equivalent implementations may be substituted for the specific embodiments shown and described without departing from the scope of the present invention. This application is intended to cover any adaptations or variations of the kind of medical devices described above. Therefore, it is intended that this invention be limited only by the claims and their equivalents.

What is claimed is:

1. A system for implanting an implantable penile prosthetic, the system comprising:
   a tool including a tube extending between a handle portion and a distal end,
      a bore formed in the tube, the bore forming a first opening at the distal end of the tube and a second opening located proximal of the distal end of the tube,
      a suture slide communicating with the bore, the suture slide having a curved surface formed between an exterior surface of the tube and the bore of the tube; and
   a first suture attached to a proximal portion of a needle, with the needle inserted in the bore with a pointed distal end of the needle closer to the first opening than to the second opening of the tube, and with a segment of the first suture inserted in the bore and alongside the needle, the first suture in contact with the suture slide, and a proximal portion of the first suture extending out of the bore at the suture slide;
   wherein the suture slide is located distal of the proximal portion of the needle that is retained in the bore;
   wherein the system is configured such that tension applied to the first suture ejects the pointed distal end of the needle out of the distal end of the tube;
   wherein the suture slide is provided as an opening formed in a wall of the tube; and
   wherein the system is characterized by an absence of a plunger inserted into the second opening of the bore.

2. The system of claim 1, wherein the suture slide is located between the proximal portion of the needle and the distal end of the bore.

3. The system of claim 1, wherein the suture slide is monolithically integrated as a part of the wall of the tube.

4. The system of claim 1, wherein the suture slide is a rotatable conveyance bar attached to the tube.

5. The system of claim 1, wherein the suture slide has a complex curvature including a first curved surface extending from the exterior surface of the tube and a second curved surface extending from the first curved surface to the bore of the tube, with a radius of curvature of the first curved surface different from a radius of curvature of the second curved surface.

6. The system of claim 1, wherein the first suture includes a single strand with one portion of the single strand inserted through an eyelet of the implantable penile prosthetic and two portions of the single strand looped through an eyelet formed in the proximal portion of the needle.

7. The system of claim 1, further comprising:
   a second suture attached to the proximal portion of the needle, the second suture placed in the bore and extending from the needle and out of the second opening formed in the tube.

8. The system of claim 7, wherein tension applied to the second suture retracts the pointed distal end of the needle back into the distal end of the tube.

9. The system of claim 1, wherein tension applied to the proximal portion of the first suture tows the proximal portion of the needle in a distal direction within the bore.

10. The system of claim 1, wherein the exterior surface of the tube includes a mark indicating a measured distance away from the distal end of the tube.

* * * * *